United States Patent [19]

Miller et al.

[11] Patent Number: 4,790,925
[45] Date of Patent: Dec. 13, 1988

[54] ELECTROCHEMICAL GAS SENSOR

[75] Inventors: Barbara C. Miller, Catonsville; RaeAnn M. Auel, Westminster; Alan A. Schneider, Reisterstown, all of Md.

[73] Assignee: Mine Safety Appliances Company, Pittsburgh, Pa.

[21] Appl. No.: 98,365

[22] Filed: Sep. 18, 1987

[51] Int. Cl.$^4$ .................. G01N 27/30; G01N 27/54
[52] U.S. Cl. ................................. 204/415; 204/408
[58] Field of Search .................. 204/415, 408, 1 K; 128/635

[56] References Cited

U.S. PATENT DOCUMENTS 4,185,620  1/1980  Hagihara .................... 128/635
4,217,196  8/1980  Huch ....................... 204/408 X

FOREIGN PATENT DOCUMENTS 2001763  2/1979  United Kingdom ............. 204/415

Primary Examiner—G. L. Kaplan

[57] ABSTRACT

Electrochemical sensor cells having reduced zero current temperature sensitivity comprise a working electrode and a counter electrode in close proximity and in contact with an electrolyte. Both electrodes are exposed to the atmosphere to be tested and at least a portion of the counter electrode is masked from the electrochemically active gas in the atmosphere.

13 Claims, 2 Drawing Sheets

ELECTROCHEMICAL GAS SENSOR

FIELD OF THE INVENTION

This invention relates to electrochemical gas sensors and in its preferred embodiment to an electrochemical cell for measurement of carbon monoxide.

BACKGROUND OF THE INVENTION

Electrochemical gas sensors are well known for determining a variety of noxious gases, including hydrogen sulfide, chlorine, nitric oxide, carbon monoxide and hydrocarbons. It is now conventional to apply the active electrode material, which may be an electrocatalyst, to a membrane that is permeable to the gas to be analyzed and is impermeable to the electrolyte. An electrochemical reaction occurs at the electrode, ordinarily called the working electrode, where the electrolyte, the active electrode material and gas diffusing through the membrane interface. An opposing counter electrode is immersed in the electrolyte and the potential or current of the cell is a measure of the gas concentration exposed to the working electrode.

UK Pat. No. 2,001,763B is a galvanic electrochemical sensor for CO in which the working electrode and counter electrode are identical noble metals in contact with an acid electrolyte, the counter electrode being immersed in the electrolyte. CO, or other depolarizing species, is measured by measuring the current or voltage across the electrodes. The cell is said to be immune to zero drift.

Such galvanic cells and other potentiostated electrochemical cells are temperature sensitive due to the change in rate of the electrochemical reaction with change in temperature in accordance with the Arrhenius equation for a simple gas reaction under kinetic control:

$$K = A \exp-(Ea/RT)$$

where K is the kinetic rate constant, A is a constant, Ea is the activation energy of the reaction, R is the gas contact and T is the absolute temperature. In practical application such as CO oxidation on platinum in sulfuric acid, this relationship is approximately correct. In a cell to sense CO in air, there is also a small oxidizing current present in the absence of any CO (zero current). The reaction or reactions causing the zero current is not totally understood but it is believed to result from oxidation of the submerged platinum electrode. Although these currents are small, they are very temperature sensitive resulting in a significant change of zero current with change in temperature. Such a zero current temperature dependence is common in electrochemical gas sensors.

SUMMARY OF THE INVENTION

This invention is based on our discovery that zero current temperature sensitivity of electrochemical sensor cells can be reduced to an extent that electronic temperature compensation is unnecessary by exposing the counter electrode to the atmosphere to be tested and masking at least a portion of the counter electrode from the electrochemically active gas in the atmosphere to be tested.

Our invention comprises an electrochemical gas sensor for determining an electrochemically active gas in the atmosphere comprising a working electrode and a counter electrode in close proximity and in contact with an electrolyte, each of said electrodes comprising an electrocatalytic material, means for exposing the working electrode and the counter electrode to the atmosphere to be tested, and masking means for preventing exposure of at least a portion of the counter electrode to the electrochemically active gas whereby the presence of electrochemically active gas in the atmosphere to be tested produces a current.

A preferred embodiment comprises a working electrode and a counter electrode deposited on one surface of a gas-permeable membrane phobic to the electrolyte. The masking means may comprise a gas-impermeable film secured to the opposite surface of the membrane over a portion of the counter-electrode sufficient to give a measurable cell output. The mask permits only a portion of the counter electrode to be exposed to gas passing through the membrane while the entire area of the electrode is exposed to the electrolyte. The cell output increases as the masked area is made larger and is the preferred embodiment. The masked area is at least equal to the unmasked area and the unmasked area is approximately equal to the area of the working electrode.

An alternative masking means comprises a cover made of gas-impervious material secured to and having a portion spaced from the opposite surface of the membrane to form a chamber between the membrane and cover extending over at least a portion of the working electrode and counter electrode, and a gas diffusion path through the cover and aligned so that the working electrode intercepts substantially all the electrochemically active gas diffusing through said diffusion path. This type of masking exposes the counter electrode to atmosphere to be tested from which at least a portion of the electrochemically active gas has been reacted. The most preferred embodiment uses both types of masking.

DETAILED DESCRIPTION OF THE INVENTION

The following detailed description is of a preferred embodiment for measuring CO in air. Other embodiments, though not described in detail, are within the scope of the invention.

Figure 1:
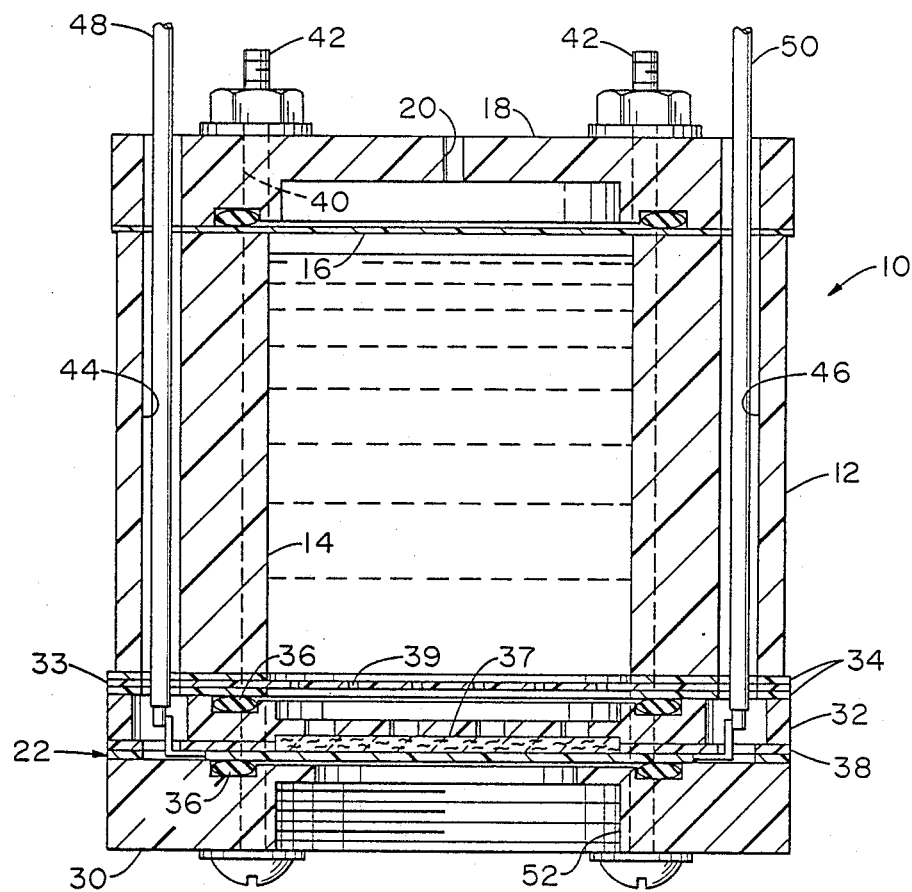
FIG. 1 is a section of a gas sensor cell of the invention.
Figure 2:
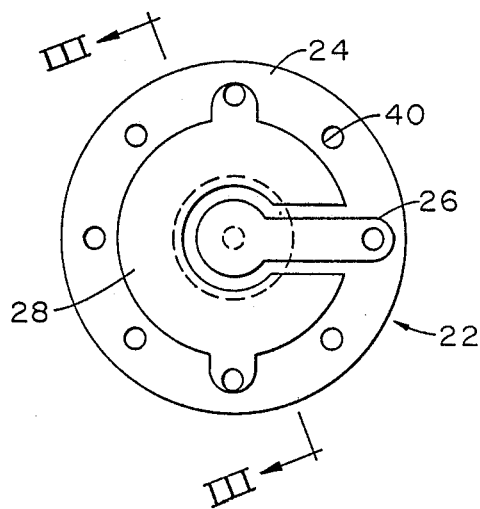
FIG. 2 is a plan view from the side exposed to electrolyte of the gas diffusion membrane electrode in the sensor cell of FIG. 1.
Figure 3:
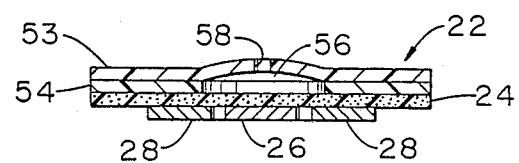
FIG. 3 is a section through line III—III of FIG. 2.

Referring to FIG. 1, FIG. 2 and FIG. 3, electrochemical cell 10 comprises a cylindrical housing 12 having a central cavity 14 containing electrolyte. The cavity is closed on one end by membrane 16 sealingly engaged between the body and endplate 18. Membrane 16 is a flexible material, to contain electrolyte and accommodate pressure changes in the cell, such as, e.g., PTFE sheet. Endplate 18 contains a relief port 20 open to the atmosphere. The electrolyte is contained at the other end by working/counter electrode 22 comprising a membrane 24 on which a platinum black working electrode 26 and counter electrode 28 are deposited. The electrode 22 is sealed to the cell body by endplate 30, electrode holder 32 and gaskets 34 and 38, and O-Rings 36. Membrane 33 has holes and serves as a baffle to diminish electrolyte sloshing. The electrode is supported by porous separator or filter 37 of glass fiber that also serves as an electrolyte wick.

The cell components are provided with holes 40 to receive mounting bolts 42. Holes 44 and 46 receive leads 48 and 50 that are electrically connected respectively to the working electrode and counter electrode. The leads are connected to an external circuit for measuring current flow between the electrodes to indicate the concentration of the gas being analyzed.

Endplate 30 has an opening 52 for exposing the electrode to the atmosphere being tested. The opening is threaded to receive, if desired, a plug (not shown) having inlet and outlet openings for flowing sample gas through the cell.

Referring to FIGS. 2 and 3, the electrode 22 includes a gas diffusion membrane 24 having a catalytic working electrode 26 and an identical catalytic counter electrode 28 bonded thereto. Membrane 24 is preferably a porous fluorocarbon membrane such as Goretex ®. Other similar membrane materials may be used that are phobic, or not wetted, by the electrolyte, having a large number of pores (e.g., 50% porous) which have a small pore size, are non-reactive with the electrolyte or atmosphere, and are thin enough to permit adequate diffusion of CO to the working electrode. The working and counter electrodes are preferably prepared by mixing a suitable catalyst with polytetrafluoroethylene (Teflon ®) dispersion and painting the mixture onto the gas diffusion membrane 24. The membrane and catalyst mixture are dried and sintered to give a good bond. The catalytic material is preferably platinum black when measuring CO, but may be other noble metals. These or other catalysts may be selected for measuring other gases in galvanic or potentiostated cells. Such catalysts include gold, silver, platinum, palladium, iridium, ruthenium, rhodium, osmium, and alloys and mixtures of these metals.

Figure 4:
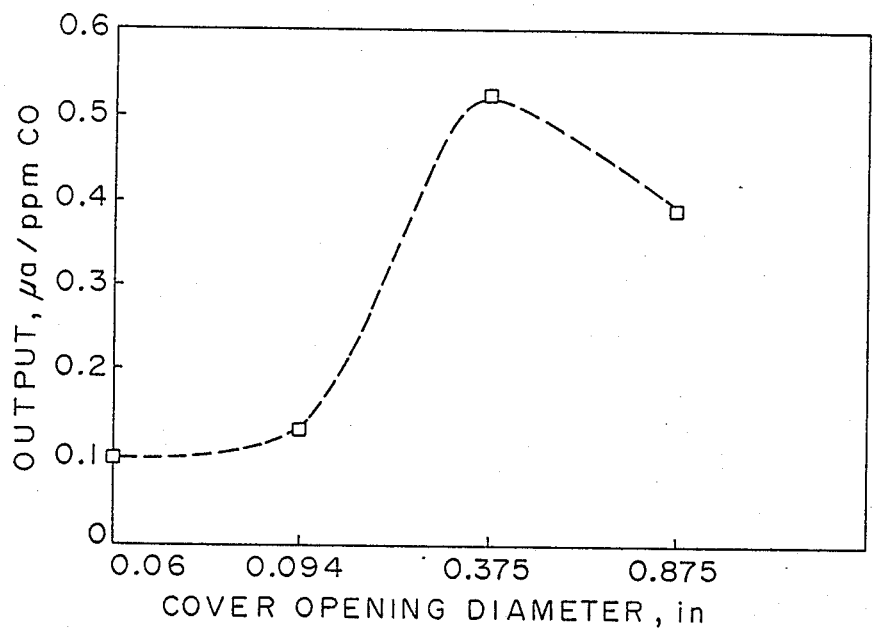
FIG. 4 is a chart of the sensitivity of the cell in relation to opening size in the electrode cover.

The electrode 22 includes a mask 54 formed of a gas-impervious film, such as, for example, 2 mil polyethylene, covering a portion of the counter electrode. The mask may also cover a portion of the working electrode to adjust the relative areas of the electrodes exposed to the atmosphere through membrane 24. The electrode may also include a cover 53, also formed of a gas-impermeable film, having a portion spaced from the membrane 24 and mask 54 to form a chamber 56. Cover 53 has an opening 58 aligned with the working electrode to restrict entrance of the atmosphere to be measured into chamber 56 for adjusting the output of the cell to a desired range compatible with the electronic measuring current and the gas concentrations to be measured. The opening may be any size, including coextensive with mask 54; as shown in FIG. 4, the cell output goes through a maximum with a change in the size of opening 58.

The film cover is flexible and resulting variations in the shape of chamber 56 have no detrimental effect so long as the cover is sized so that the gas diffusing through the opening 58 first contacts the working electrode. Gas diffuses into and through chamber 56, to the portion of the diffusion membrane on which the working electrode is deposited, and then through the membrane 24 where the reactive gas is electrochemically oxidized. The counter electrode, being outside this diffusion path is exposed to the same atmosphere within chamber 56 as the working electrode, except for the removed electrochemically reacted gas. In the preferred cell for measuring CO, the working and counter electrodes are of identical (platinum black) material and have identical areas exposed to chamber 56 through membrane 24. The area of the working electrode is preferred to be sufficient to react substantially all the CO reaching it, although incomplete reaction is permissible with a resultant loss of signal magnitude. The relative area of the two electrodes can be modified to account for varying activity when the two electrodes are made of different materials or maintained at different potentials, or to adjust for IR drop if the electrodes are more widely spaced.

Figure 5:
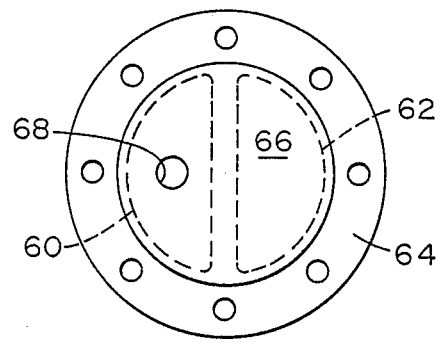
FIG. 5 is a plan view of an alternate electrode.

An alternate construction is shown in FIG. 5 in which no mask like mask 54 is used; i.e. the entire area of the counter electrode is exposed to the atmosphere through the membrane. The working electrode 60 and counter electrode 62 are of equal area and bonded to one surface of gas-permeable membrane 64. Cover 66 is laminated to the membrane to form a chamber between the cover and membrane with an opening 68 aligned with the center of the working electrode. This cell has an output about one-half that of the cell of FIG. 2, but does have flat zero temperature characteristics.

The cells of this invention, in addition to being resistant to zero drift, show little change of zero or base current with temperature change, thus avoiding the need to measure cell temperature and make corrections for zero current changes. Illustrative of the invention, five cells configured as FIGS. 1-3, were made in which the working electrode and counter electrode were platinum black, each with a geometric area of 1.1 cm$^2$. The diffusion opening in the electrode cover was 0.06 inches in diameter. Table 1 is a chart of zero current (expressed as ppm of CO corresponding to the zero current) for cell temperature, for cells run through temperature cycling indicated by reading from the top to the bottom of the table. Zero current is expressed as the ppm CO signal equivalent to the zero amount.

TABLE I

| Temperature (0° C.) | Zero Current (equivalent ppm CO) Cell # | | | | |
|---|---|---|---|---|---|
| | 1 | 2 | 3 | 4 | 5 |
| 24 | 0.7 | 0.0 | 1.6 | 1.1 | 1.3 |
| 1 | 0.9 | 0.0 | 0.7 | 0.0 | 0.8 |
| 40 | 1.8 | 0.0 | 4.9 | 3.1 | 0.6 |
| 24 | 1.4 | −0.6 | 1.6 | 1.2 | 0.7 |
| 11 | 0.8 | 0.0 | 0.6 | 0.6 | 0.7 |
| 30 | 1.9 | 0.0 | 2.1 | 2.2 | 1.3 |

COMPARATIVE EXAMPLES

Conventional CO sensor cells with a platinum black working electrode and a platinum black counter electrode immersed in electrolyte were temperature cycled as indicated in Table II. Cells numbered 1 and 2 were potentiostated at 150 mv. and cells 3-6 were galvanic cells. Table II shows the variation in zero current.

TABLE II

| Temperature (0° C.) | Zero Current (equivalent ppm CO) Cell # | | | | | |
|---|---|---|---|---|---|---|
| | 1 | 2 | 3 | 4 | 5 | 6 |
| 24 | 7.9 | 7.2 | 2.8 | 1.8 | 0.9 | 2.5 |
| −1 | 4.1 | 3.8 | 1.1 | 0.9 | 0.0 | 1.9 |
| 40 | 16.3 | 16.3 | 14.0 | 7.5 | 4.4 | 5.4 |

TABLE II-continued

| Temperature (0° C.) | Zero Current (equivalent ppm CO) Cell # | | | | | |
| --- | --- | --- | --- | --- | --- | --- |
| | 1 | 2 | 3 | 4 | 5 | 6 |
| 24 | 7.8 | 7.7 | | | | |
| 12 | 5.0 | 5.1 | | | | |
| 14 | | | | | 1.8 | 1.7 |
| 31 | 10.9 | 10.9 | | | | |
| 32 | | | | | 2.6 | 2.5 |

We claim:

1. A gas sensor for determining an electrochemically active gas in the atmosphere comprising a working electrode and a counter electrode in contact with an electrolyte, the working electrode and counter electrode being bonded in close proximity on one surface of a gas-permeable membrane phobic to the electrolyte, each of said electrodes comprising a catalytic metal, means for exposing the working electrode and the counter electrode to the atmosphere to be tested and masking means for preventing exposure of at least a portion of the counter electrode to the electrochemically active gas, whereby the presence of electrochemically active gas in the atmosphere to be tested produces a current.

2. A sensor of claim 1 in which the working electrode and counter electrode are of identical composition.

3. A sensor of claim 2 in which the masking means comprises a gas-impermeable film secured to the opposite surface of the membrane over a portion of the counter electrode.

4. A sensor of claim 3 in which the masking means comprises a cover means secured to and having a portion spaced from the opposite surface of the membrane to form a chamber between the membrane and cover extending over at least a portion of the working electrode and counter electrode, a gas diffusion path through the cover and situated so that the working electrode intercepts substantially all the electrochemically active gas diffusing through said diffusion path.

5. A sensor of claim 4 in which the working electrode and counter electrode are of identical composition and have equal areas exposed to the atmosphere.

6. A sensor of claim 5 for measuring carbon monoxide in which the electrodes are platinum.

7. A sensor of claim 1 in which the masking means comprises a cover means secured to and having a portion spaced from the opposite surface of the membrane to form a chamber between the membrane and cover extending over at least a portion of the working electrode and counter electrode, a gas diffusion path through the cover and situated so that the working electrode intercepts substantially all the electrochemically active gas diffusing through said diffusion path.

8. A sensor of claim 1 in which the electrodes are platinum.

9. An electrode assembly for an electrochemical gas sensor comprising a working electrode and a counter electrode of catalytic metal deposited in close proximity on one surface of a gas-permeable membrane, and a gas-impermeable film secured to the opposite surface of the membrane over a major portion of the counter electrode.

10. An electrode assembly for an electrochemical gas sensor comprising a working electrode and a counter electrode of catalytic metal deposited in close proximity on one surface of a gas-permeable membrane, and a cover means secured to and having a portion spaced from the opposite surface of the membrane to form a chamber between the membrane and cover extending over at least a portion of the working electrode and counter electrode, a gas diffusion opening through the cover and aligned with the working electrode so that substantially all the gas diffusing through said diffusion path is exposed to the working electrode.

11. An assembly for an electrochemical gas sensor comprising a working electrode and a counter electrode of catalytic metal deposited in close proximity on one surface of a gas-permeable membrane, gas impermeable masking means secured to the opposite surface of said membrane, said masking means masking a major portion of the counter electrode and having a portion spaced from the opposite surface of the membrane to form a chamber between the membrane and cover extending over at least a portion of the working electrode and counter electrode, and a gas diffusion opening through the cover and aligned with the working electrode so that substantially all the gas diffusing through said diffusion path is exposed to the working electrode.

12. An assembly of claim 11 in which the electrodes are of identical composition and the areas of each electrode exposed to the chamber are equal.

13. An assembly of claim 12 in which the electrodes are platinum.

* * * * *